United States Patent [19]

Okuda et al.

[11] Patent Number: 4,654,206

[45] Date of Patent: Mar. 31, 1987

[54] FAST RELEASE SOLID PREPARATION OF DIHYDROPYRIDINE A COMPOUND

[75] Inventors: Kiyoshi Okuda, Otsu; Renji Aoi, Osaka, both of Japan

[73] Assignee: Fujisawa Pharmaceutical Co., Ltd., Osaka, Japan

[21] Appl. No.: 634,431

[22] Filed: Jul. 26, 1984

[30] Foreign Application Priority Data

Aug. 11, 1983 [JP] Japan .................. 58-147871

[51] Int. Cl.⁴ .................. A61K 9/28; A61K 9/20; A61K 9/26
[52] U.S. Cl. .................. 424/480; 514/344; 514/781; 514/946
[58] Field of Search .................. 514/344, 781, 946; 424/16, 78

[56] References Cited

U.S. PATENT DOCUMENTS

| | | | |
|---|---|---|---|
| 3,852,421 | 12/1974 | Koyanagi et al. | 514/781 |
| 4,259,314 | 3/1981 | Lowey | 514/781 |
| 4,265,875 | 5/1981 | Byrne et al. | 514/781 |
| 4,369,172 | 1/1983 | Schor et al. | 514/781 |
| 4,389,393 | 6/1983 | Schor et al. | 514/781 |
| 4,412,986 | 11/1983 | Kawata et al. | 424/80 |

FOREIGN PATENT DOCUMENTS

| | | |
|---|---|---|
| 3307422 | 9/1984 | Fed. Rep. of Germany ...... 514/344 |
| 58-77811 | 5/1983 | Japan . |
| 58-109412 | 6/1983 | Japan . |
| 2050828 | 1/1981 | United Kingdom . |
| 2053681 | 2/1981 | United Kingdom . |
| 2111386 | 7/1983 | United Kingdom . |
| 2122085 | 1/1984 | United Kingdom . |

*Primary Examiner*—Ronald W. Griffin
*Attorney, Agent, or Firm*—Oblon, Fisher, Spivak, McClelland & Maier

[57] ABSTRACT

This invention relates to a fast release solid preparation, which comprises a solid dispersion composition containing dihydropyridien A compound uniformly dispersed in hydroxypropylmethyl cellulose as the dispersion medium, said dihydropyridine A compound being maintained in the amorphous state in said solid dispersion composition.

4 Claims, No Drawings

FAST RELEASE SOLID PREPARATION OF DIHYDROPYRIDINE A COMPOUND

The present invention relates to the fast release solid preparation comprising dihydropyridine A compound [isopropyl 6-cyano-5-methoxycarbonyl-2-methyl-4-(3-nitrophenyl)-1,4-dihydropyridine-3-carboxylate], which is represented by the following chemical formula:

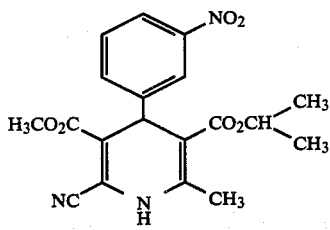

Dihydropyridine A compound shows vasodilating activities such as coronary vasodilating activity, hypotensive activity or the like, and hence is useful for the treatment of coronary vascular diseases such as cardiac incompetence, angina pectoris, myocardial infarction or the like, or hypertension.

However, when orally administered, the ratio of the absorption of dihydropyridine A compound into blood to its dose is insufficient owing to its sparing solubility into water (practically insoluble) and so dihydropyridine A compound has the disadvantage of its poor bioavailability.

The inventors of the present invention have discovered that said disadvantage could be overcome by dispensing dihydropyridine A compound with hydroxypropylmethyl cellulose, a water-soluble polymer, to prepare solid dispersion composition and completed the present invention.

The present invention is explained in more detail in the following.

The solid dispersion composition of the present invention can be prepared, for example, by dissolving dihydropyridine A compound in suitable organic solvent, adding a water-soluble polymer, hydroxypropylmethyl cellulose, to the resultant solution to prepare homogeneous suspension, and then evaporating the organic solvent according to the conventional manner.

The organic solvents to be used in this procedure are not restrictive and any solvent, wherein dihydropyridine A compound can be dissolved, can be used. Suitable examples of said solvent may include chloroform, methylene chloride, acetone, ethyl acetate, alcohol (e.g. methanol, ethanol, etc.) and the like.

Hydroxypropylmethyl cellulose is one of the water-soluble polymers and it is used to disperse dihydropyridine A compound to form solid dispersion composition.

The quantity of hydroxypropylmethyl cellulose to be used is not restrictive and any quantity, by which dihydropyridine A compound can be dispersed, can be used and preferably three to seven times as much as dihydropyridine A compound by weight are used.

The solid dispersion composition of the present invention prepared by aforesaid procedure can be used by itself as fast release solid preparation and may be converted into various dosage forms such as powders, fine granules, granules, tablets or the like, according to the conventional manner. If desired, coloring agents, sweetening agents, flavouring agents, diluents (e.g. sucrose, lactose, starch, crystalline cellulose, low-substituted hydroxypropyl cellulose, synthetic aluminium silicate, etc.), lubricant (e.g. magnesium stearate, etc.) or the like, may be dispensed with said solid dispersion composition.

The solid dispersion composition and the various preparations of the present invention, which are prepared by optionally converting said solid dispersion composition into various dosage forms as mentioned above, have remarkably improved solubility and absorptivity into blood in comparison with dihydropyridine A compound bulk.

If desired, in order to enhance the stability, add a beauty, smooth the surface, improve the ease of the administration and the like, the solid dispersion composition as prepared above can be used, for example, as a film-coated tablet.

Said film-coated tablet can be prepared by coating the aforementioned tablet according to the conventional method, wherein the coating layer may include hydroxypropylmethyl cellulose.

To show the usefulness of the fast release solid preparation of the present invention, the test results are explained as follows.

Dissolution Test

[Test Sample]

(1) The fine granules disclosed in the following Example 2
(2) The tablet disclosed in the following Example 3
(3) The film-coated tablet disclosed in the following Example 4.

[Test Method]

The tests were carried out according to the method 2 (paddle method) of the dissolution test in The Pharmacopoeia of Japan (tenth edition) using water as test solution and the dissolution rate after 15 minutes from the beginning of each dissolution test was measured.

[Test Results]

| Test Sample | Dissolution rate (%) |
|---|---|
| (1) | 100 |
| (2) | 100 |
| (3) | 100 |

From the results of the dissolution test, it turned out that any solid preparation comprising the solid dispersion composition of dihydropyridine A compound exhibited extremely good dissolution velocity.

Plasma Concentration Test

[Test Sample]

(1) The tablet disclosed in the following Example 3 (This tablet contains 2 mg of dihydropyridine A compound in one tablet.)
(2) The reference tablet: Tablets, each of which had the composition as explained below, were prepared by the conventional method (wet granulating method) and they were used as the reference tablets in this test.

Composition

Dihydropyridine A compound (micro power): 10 mg
Lactose: 88.5 mg

Low-substituted hydroxypropyl cellulose: 30 mg
Sodium lauryl sulfate: 3 mg
Hydroxypropylmethyl cellulose: 3 mg
Magnesium stearate: 0.5 mg

[Test Method]

The amount of tablets equivalent to 10 mg of dihydropyridine A compound [i.e. 5 tablets of Test Sample (1) and 1 tablet of Test Sample (2)] was orally administered to six beagle dogs (8–12 kg), which had been withheld from any food overnight in a crossover design. The plasma concentration of dihydropyridine A compound was determined by gas chromatography with ECD at 0.5, 1, 2, 4, 6, 8, 10, 12 and 24 hours after administration.

[Test Results]

The plasma concentration at each time, the maximum plasma concentration (C max) and the area under the plasma concentration time curve (AUC) in each case of Test Sample (1) and Test Sample (2) are shown in the following table.

Each value is represented by [the mean value±standard error] for six beagle dogs.

| Test Sample | Plasma concentration (ng/ml) | | | | | | | | | C max (ng/ml) | A U C (ng · hr/ml) |
|---|---|---|---|---|---|---|---|---|---|---|---|
| | 0.5 hr | 1 hr | 2 hr | 4 hr | 6 hr | 8 hr | 10 hr | 12 hr | 24 hr | | |
| (1) | 133.6 | 95.1 | 45.8 | 19.6 | 12.7 | 9.6 | 7.7 | 6.9 | 1.2 | 133.6 | 361.1 |
| | ±20.4 | ±10.4 | ±5.0 | ±2.7 | ±1.8 | ±1.5 | ±1.1 | ±1.1 | ±0.6 | ±20.4 | ±47.4 |
| (2) | 34.1 | 59.8 | 41.0 | 17.6 | 10.8 | 7.3 | 5.9 | 4.3 | 0.3 | 59.8 | 238.9 |
| | ±6.4 | ±7.2 | ±6.5 | ±2.1 | ±1.3 | ±0.9 | ±0.8 | ±0.6 | ±0.3 | ±7.2 | ±27.2 |

As clear from the table, with respect to both the maximum plasma concentration and the area under the plasma concentration time curve, Test Sample (1) was proved to be significantly superior to Test Sample (2).

Namely, it turned out that by dispensing dihydropyridine A compound with hydroxypropylmethyl cellulose to form solid dispersion composition, the absorptivity of dihydropyridine A compound into blood was remarkably improved and that its bioavailability was extremely enhanced.

The present invention is explained according to the following Examples.

EXAMPLE 1

Dihydropyridine A compound (100 g) was dissolved in anhydrous ethanol (5 l) and then hydroxypropylmethyl cellulose (500 g) was added thereto to prepare a suspension. Then the organic solvent was evaporated under reduced pressure to give solid dispersion composition.

EXAMPLE 2

To a suspension of dihydropyridine A compound (100 g) and hydroxypropylmethyl cellulose (500 g) in anhydrous ethanol (5 l) was added sucrose (9.4 kg) and the resultant mixture was stirred. Then the organic solvent was evaporated under reduced pressure to give solid dispersion composition.

This solid dispersion composition was converted into fine granules by the conventional method.

EXAMPLE 3

To a suspension of dihydropyridine A compound (100 g), and hydroxypropylmethyl cellulose (500 g) in anhydrous ethanol (5 l) were added lactose (6.87 kg) and low-substituted hydroxypropyl cellulose (1.5 kg) and the resultant mixture was stirred and then the organic solvent was evaporated under reduced pressure to give solid dispersion composition.

After the resultant solid dispersion composition was converted into granules by the conventional method, the granules were converted with magnesium stearate (30 g) into tablets by the conventional method, each weight of which was 180 mg.

EXAMPLE 4

For each tablet given in the Example 3, the coating layer consisting of hydroxypropylmethyl cellulose (5.1 mg), titanium dioxide (1.6 mg), polyethylene glycol-6000 (0.8 mg), talc (0.4 mg) and iron oxide yellow (0.1 mg) was film-coated by the conventional method, to give a film-coated tablet containing dihydropyridine A compound.

What we claim is:

1. A fast release solid preparation, which comprises a solid dispersion composition containing dihydropyridine A compound uniformly dispersed in hydroxypropylmethyl cellulose as the dispersion medium, said dihydropyridine A compound being maintained in the amorphous state in said solid dispersion composition.

2. The fast release solid preparation of claim 1, wherein the dosage form is a tablet.

3. The tablet of claim 2, wherein its surface is film-coated.

4. The fast release solid preparation of claim 1, wherein dihydropyridine A compound and hydroxypropylmethyl cellulose are in the ratio of 1:3 to 1:7 by weight.

* * * * *